(12) United States Patent
Cole

(10) Patent No.: US 11,860,139 B2
(45) Date of Patent: Jan. 2, 2024

(54) SYSTEM AND METHOD FOR ANALYSING THE COMPOSITION OF A QUENCHED FLOW REACTION LIQUID

(71) Applicant: Applied Photophysics Limited, Leatherhead (GB)

(72) Inventor: Lindsay John Cole, Leatherhead (GB)

(73) Assignee: Applied Photophysics Limited, Leatherhead (GB)

( * ) Notice: Subject to any disclaimer, the term of this patent is extended or adjusted under 35 U.S.C. 154(b) by 0 days.

(21) Appl. No.: 17/283,523

(22) PCT Filed: Oct. 7, 2019

(86) PCT No.: PCT/GB2019/052818
§ 371 (c)(1),
(2) Date: Apr. 7, 2021

(87) PCT Pub. No.: WO2020/074863
PCT Pub. Date: Apr. 16, 2020

(65) Prior Publication Data
US 2022/0003725 A1    Jan. 6, 2022

(30) Foreign Application Priority Data
Oct. 8, 2018  (GB) ..................... 1816309

(51) Int. Cl.
*G01N 30/24*     (2006.01)
*G01N 30/72*     (2006.01)
(Continued)

(52) U.S. Cl.
CPC ......... *G01N 30/7233* (2013.01); *G01N 30/24* (2013.01); *G01N 2030/027* (2013.01); *G01N 2030/347* (2013.01)

(58) Field of Classification Search
CPC ............... G01N 30/7233; G01N 30/24; G01N 2030/027; G01N 2030/347; G01N 30/72;
(Continued)

(56) References Cited

U.S. PATENT DOCUMENTS 4,778,751 A * 10/1988 El Shami ............. G01N 33/531
436/538
4,863,876 A *  9/1989 Hevey .................. G01N 33/542
436/546
(Continued)

FOREIGN PATENT DOCUMENTS

| WO | 2007124332 A1 | 11/2007 |
| WO | 2012167273 A2 | 12/2012 |
| WO | 2015184430 A1 | 12/2015 |

OTHER PUBLICATIONS

Jingxi Pan, et al., "Hydrogen/Deuterium Exchange Mass Spectrometry with Top-Down Electron Capture Dissociation for Characterizing Structural Transitions of a 17 kDa Protein", Journal of the American Chemical Society, vol. 131, No. 35, Sep. 9, 2009.
(Continued)

*Primary Examiner* — David J Bolduc
(74) *Attorney, Agent, or Firm* — ArentFox Schiff LLP

(57) ABSTRACT

The present invention relates to a system for analysing the composition of a quenched flow reaction liquid comprising a quenched flow reactor, and a high performance liquid chromatography (HPLC) apparatus; wherein the quenched flow reactor is in fluid communication with the HPLC apparatus.

15 Claims, 7 Drawing Sheets

(51) Int. Cl.
  *G01N 30/02* (2006.01)
  *G01N 30/34* (2006.01)
(58) Field of Classification Search
  CPC ......... G01N 33/6848; G01N 2030/067; G01N 2030/207; G01N 2030/8831
  See application file for complete search history.

(56) References Cited

U.S. PATENT DOCUMENTS

| | | | |
|---|---|---|---|
| 6,350,987 B1 | 2/2002 | Northrup et al. | |
| 2002/0022802 A1* | 2/2002 | Simpson | B01L 3/0227 128/DIG. 1 |
| 2004/0132215 A1* | 7/2004 | Lackie | G01N 21/6428 436/518 |
| 2005/0048581 A1* | 3/2005 | Chiu | B01L 3/502784 435/7.1 |
| 2005/0233406 A1* | 10/2005 | Woods, Jr. | G01N 33/6848 435/23 |
| 2006/0226082 A1* | 10/2006 | Brook | G01N 30/50 435/7.1 |
| 2007/0110619 A1* | 5/2007 | Adler | B01J 19/087 422/78 |
| 2010/0011262 A1 | 5/2010 | Emmett et al. | |
| 2011/0027815 A1* | 2/2011 | Salomon | C12Q 1/61 435/18 |
| 2011/0314900 A1* | 12/2011 | Blacklin | G01N 30/02 73/61.55 |
| 2011/0318243 A1* | 12/2011 | Blacklin | G01N 1/2035 422/501 |
| 2012/0231486 A1 | 9/2012 | Lavold et al. | |
| 2012/0245857 A1* | 9/2012 | Lee | G01N 33/6848 702/22 |
| 2013/0071867 A1* | 3/2013 | Fadgen | C12M 45/09 435/23 |
| 2014/0030751 A1* | 1/2014 | Sharp | G01N 33/6848 435/23 |
| 2015/0111787 A1* | 4/2015 | Shen | G01N 35/1095 506/37 |
| 2015/0204893 A1* | 7/2015 | Karlsen | G01N 33/94 250/282 |
| 2015/0346170 A1* | 12/2015 | Huang | G01N 30/84 436/500 |
| 2016/0077061 A1* | 3/2016 | Cormier | G01N 30/20 73/61.55 |
| 2016/0123991 A1* | 5/2016 | Mumm | G01N 33/6848 435/23 |
| 2016/0195564 A1* | 7/2016 | Hewitson | G01N 30/06 422/63 |
| 2016/0219910 A1* | 8/2016 | Silver | A61P 1/16 |
| 2016/0223530 A1* | 8/2016 | Marshall | G01N 30/72 |
| 2018/0149625 A1* | 5/2018 | Hewitson | G01N 30/06 |
| 2019/0041332 A1* | 2/2019 | Thomas | G01N 33/5308 |

OTHER PUBLICATIONS

International Search Report and Written Opinion for PCT/GB2019/052818, dated Jan. 24, 2020, 12 pages.

"Quench-Flow Instrument RQF-3 Rapid", Kin Tek Corporation, 2020, retrieved at https://kintekcorp.com/rqf-3, 4 pages.

Tenson, T., et al, "The Mechanism of Action of Macrolides. Lincosamides and Streptogramin B Reveals the Nascent Peptide Ex.it Path in the Ribosome" Journal of Molecular Biology, vol. 330, No. 5, 2003, pp. 1005-1014.

Amornwatcharapong, W. et al, "Human and Plasmodium serine hydroxymethyltransferases differ in rate limiting steps and pH-dependent substrate inhibition behaviour", Archives of Biochemistry and Biophysics, vol. 630, 2017, pp. 91-100.

Chenprakhon, P., et al, "Hydroxylation of 4-hydroxyphenylethylamine derivatives by R263 variants of the oxygenase component ofp-hydroxyphenylacetate-3-hydroxylase", Archives of Biochemistry and Biophysics, vol. 620, 2017, pp. 1-11.

GB Search Report for British Patent Application No. 1816309.7, dated Dec. 7, 2018, 2 pages.

Bertoldi, M., et al., "Reactions of human liver peroxisomal alanine: glyoxylate aminotransferase with beta-chloro-L-alanine and L-cysteine: Spectroscopic and kinetic analysis", Biochinica et Biophysica Acta, vol. 1784, No. 9, 2008, pp. 1356-1362.

* cited by examiner

SYSTEM AND METHOD FOR ANALYSING THE COMPOSITION OF A QUENCHED FLOW REACTION LIQUID

CROSS-REFERENCE TO RELATED APPLICATIONS:

This application is a National Phase of PCT/GB2019/052818, filed on Oct. 7, 2019, which claims priority to GB Patent Application No. 1816309.7, filed on Oct. 8, 2018, the disclosures of which are hereby incorporated by reference in their entireties.

The present invention relates to a system and method for analysing the composition of a quenched flow reaction liquid, and in particular to the preparing and analysing a quenched flow reaction liquid by high performance liquid chromatography (HPLC).

It is known to use a robotic sample handling system with a liquid chromatography mass spectrometer to analyse proteins by labelling the protein, or inducing a measurable change in the protein, such as by using deuterium oxide, and stopping this change by addition of a quenching reagent at a defined time point, known as Hydrogen Deuterium Exchange (HDX). The quenched protein sample is then transferred by the robotic system to a HPLC apparatus due to the pressure differences between the quenched flow reactor and the HPLC apparatus. This system is only able to prepare defined quench labelled protein at defined time points longer than 30 seconds.

It is also known to use a quenched flow reaction to analyse proteins by labelling the protein, or inducing a measurable change in the protein, such as by using deuterium oxide and then in a flow line the labelling is stop by mixing with a solution that quenches that stops the labelling reaction on timescales of milliseconds to seconds. The quenched flow reaction output is then manually transferred to a HPLC apparatus due to the pressure differences between the quenched flow reactor and the HPLC apparatus. This manual intervention means that the process is not automated, which reduces the throughput of proteins to be analysed. This manual intervention also increases the variability of the time between the quenched protein sample being produced and being loaded into the HPLC apparatus, which causes variability in the analysis output. This is particularly the case when the reaction is not completely quenched, such as when using deuterium oxide as the manual intervention is not consistently replicated.

Further, there is a desire to have fast reaction times, such as reactions taking milliseconds in order to review the structure of molecules, such as proteins, to give closer control of the reaction and more information about the surface structure of the molecule. Fast HDX is a particularly desirable analysis technique, in particular Fast HDX in combination with HPLC and mass spectroscopy.

Further there is a need to increase the throughput of analysis to maximise the use of the equipment and the number of results produced and improve the reproducibility of the results produced.

It is, therefore, an object of the present invention to seek to alleviate the above identified problems.

SUMMARY OF THE INVENTION

According to one aspect of the present invention, there is provided a system for analysing the composition of a quenched flow reaction liquid comprising a quenched flow reactor, and a high performance liquid chromatography (HPLC) apparatus; wherein the quenched flow reactor is in fluid communication with the HPLC apparatus.

In another aspect of the present invention, there is provided a method for analysing the composition of a quenched flow reaction liquid comprising:
  (a) providing a first reagent,
  (b) providing a second reagent,
  (c) mixing the first reagent and the second reagent in a reaction area,
  (d) allowing a reaction to take place between the first reagent and the second reagent in the reaction area for a predetermined reaction time,
  (e) quenching the reaction in a quenching area to form a quenched flow reaction liquid,
  (f) directly transferring a proportion of the quenched flow reaction liquid into a HPLC apparatus, and
  (g) analysing the quenched flow reaction liquid by HPLC to form an HPLC analyte.

DETAILED DESCRIPTION

The present invention relates to a system for analysing the composition of a quenched flow reaction liquid comprising a quenched flow reactor, and a high performance liquid chromatography (HPLC) apparatus; wherein the quenched flow reactor is in fluid communication with the HPLC apparatus. An advantage of the system is that it allows the analysis process to be fully automated. This increases the capacity of the equipment to analyse quenched flow reaction liquids as the reactions can be automated and no manual step is required to transfer the quenched flow reaction liquid to the HPLC apparatus. Furthermore, reaction times of the order of milliseconds are achievable. Further the process is more efficient due to the direct fluid communication between the devices which increases the equipment throughput. Further the automation improves the consistency of the analysis.

It will be understood that fluid communication has the normal meaning, that the quenched flow reactor is directly connected to the HPLC apparatus, such that fluid can flow directly from the quenched flow reactor into the HPLC apparatus when any valves are arranged in the required position.

Preferably the quenched flow reactor comprises:
  (i) a first reagent release mechanism,
  (ii) a second reagent release mechanism,
  (iii) a reaction area,
  (iv) a quenching reagent release mechanism, and
  (v) a quenching area.

Preferably the first reagent release mechanism is automated. Preferably the second reagent release mechanism is automated. Preferably the quenching reagent release mechanism is automated. Preferably the first reagent release mechanism, the second reagent release mechanism and the quenching reagent release mechanism are each automated. Automation allows the operator to program the required reagent release start and end time, together with the release rate to accurately carry out the reaction. Further this allows a reaction time of the order of milliseconds to be achieved. Further this allows efficient use of the equipment. Further this leads to reproduceable results as the time from the reaction starting, to the reaction being quenched, to the analysis stage is consistent.

Preferably the first reagent release mechanism is a syringe. Preferably the second reagent release mechanism is a syringe. Preferably the quenching reagent release mechanism is a syringe. Preferably the first reagent release mechanism, the second reagent release mechanisms and the quenching release mechanism are each a syringe. A syringe allows controlled release of each reagent in a predetermined manner and the rate of release to be controlled. Further this allows a reaction time of the order of milliseconds to be achieved.

Preferably the first reagent release mechanism, the second reagent release mechanisms and the quenching reagent release mechanism each independently comprise a syringe actuated by a stepper-motor control drive. This provides a suitable way of actuating the syringe.

Alternatively, the first reagent release mechanism may be an injector valve. The second reagent release mechanism may be an injector valve. The quenching reagent release mechanism may be an injector valve. In some embodiments each of the first reagent release mechanism, the second reagent release mechanism and the quenching reagent release mechanism is an injection valve. An injector valve provides an efficient way to introduce different reagents into the system. In particular, where several samples need to be analysed, it can be preferable for the first reagent release mechanism to be an injection valve. This allows the first reagent to be change efficiently.

Preferably the first reagent release mechanism comprises a prereaction system, preferably wherein the prereaction system comprises first precursor release mechanism, a second precursor mechanism and a prereaction area. This allows two different reactions to take place, a first reaction between a first precursor and a second precursor to form a first reagent and a second reaction between the first reagent and the second reagent. Preferably the prereaction area has one or more features of the reaction area as described herein. Preferably the first precursor release mechanism has one or more features of the first reagent release mechanism as described herein. Preferably the second precursor release mechanism has one or more features of the second reagent release mechanism as described herein.

Preferably the HPLC apparatus comprises a HPLC injection valve and a column, preferably wherein the column is a digestion column. Preferably the digestion column is a pepsin column. A digestion column allows macromolecules, such as proteins to be digested for analysis.

The HPLC injection valve allows the pressure of the quenched flow reaction liquid to be changed from low pressure, such as about 0 psi to about 200 psi in the quenched flow reactor, to higher pressure, such as about 2,000 psi to about 20,000 psi in the column of the HPLC apparatus. The pressure differential between the two apparatus is necessary for each to carry out their normal function.

Preferably the HPLC injection valve comprises a HPLC injection valve loop for holding a proportion of the quenched flow reaction liquid prior to injecting the proportion of the quenched flow reaction liquid into the column. This allows the operator to select the proportion of the quenched flow reaction liquid to be analysed. The HPLC injection valve loop can then be moved inline with the solvent of the HPLC apparatus to push the proportion of the quenched flow reaction liquid onto the column for analysis.

Preferably the diameter of the bore of the HPLC injection valve loop is about 0.05 mm to about 0.5 mm, preferably about 0.1 mm to about 0.4 mm, preferably about 0.2 to about 0.3 mm. Such diameters are suitable to withstand the high pressure required for the column, such as about 2,000 to about 20,000 psi.

Preferably the quenched flow reactor and the HPLC apparatus are connected by a bypass valve. Preferably wherein in a first position, the bypass valve directs a first proportion of the quenched flow reaction liquid to a non-HPLC apparatus location and wherein in a second position, the bypass valve directs a second proportion of the quenched flow reaction liquid into the HPLC apparatus, preferably into a HPLC injection valve. This allows the operator to direct part of the quenched flow reaction liquid that does not need to be analysed out of the system, when the bypass valve is in a first position. This allows a high flow rate to be used in the quenched flow reactor, such as about 0.2 ml/s to about 30 ml/s, preferably about 0.5 ml/s to about 20 ml/s whilst the reaction is taking place, and allows the first proportion of the quenched flow reaction liquid to be removed from the system at such a high flow rate while minimising any back pressure in the system. Preferably the first proportion of the quenched flow reaction liquid is removed via tubing with a wide bore, preferably about 0.5 mm to about 1.5 mm. Preferably the non-HPLC location is to waste. Alternatively the non-HPLC location is to a container and the first proportion of the quenched flow reaction liquid is further used, such as for analysis.

The bypass valve can then be moved into a second position which directs the second proportion of the quenched flow reaction liquid into the HPLC apparatus, preferably the HPLC injection valve, and in particular into the HPLC injection valve loop. The HPLC injection valve loop preferably has a smaller bore than that of the reaction area, such as the tube in the quenched flow reactor. This is due to the higher pressure required for the HPLC apparatus. The flow rate through the HPLC apparatus is preferably about 5 µl/s to about 250 µl/s, preferably about 10 µl/s to about 100 µl/s which is considerably lower than the flow rate through the quenched flow reactor when the reaction is occurring. It is therefore preferable for the flow rate through the system to be about 0.2 ml/s to about 30 ml/s, such as about 0.5 ml/s to 20 ml/s up until the reagents have mixed, preferably until the reaction is quenched, with the bypass valve in the first position to remove the first proportion of the quenched flow reaction liquid. It is preferable for the flow rate through the system to be about 5 µl/s to about 250 µl/s, preferably about 10 µl/s to about 100 µl/s after the reaction has been quenched, with the bypass valve in the second position to load the second proportion of the quenched flow reaction liquid into the HPLC injection valve loop, ready for analysis. The bypass valve has the advantage of allowing fast flow rates while the reaction is occurring, with lower flow rates to load the HPLC injection valve loop.

Preferably about 5% to about 80% by volume of the quenched flow reaction liquid is directed into the HPLC apparatus, preferably about 10% to about 50% by volume. Such amounts are suitable to ensure that the quenched flow reaction liquid of an accurate reaction time and first reagent to second reagent ratio enters the HPLC apparatus.

Preferably the reaction area comprises a tube. An advantage of tube is that it allows controlled mixing of the first and second reagents and the reaction can flow along the tube to be quenched. This means that the reaction will be aged in a controlled manner, as the first and second reagents are continuously released into the tube at a known rate. A tube also allows the result of the reaction to be quenched after a predetermined time as the reaction occurs along the tube. Preferably the reaction area comprises a mixer and a tube.

Preferably the mixer is at the start of the tube. The mixer may be any fluid mixer, such as a t format mixer or a berger ball (Ref:] R. L. Berger, B. B. H. F. Chapman, Rev. Sci. Instrum. 39 (1968) 493-498). The combination of a mixer and a tube helps the reaction to be carried out in a controlled manner.

Preferably the length of the tube can be varied. Varying the length of the tube means that the length of the reaction time can be easily changed as the reaction area is shortened or lengthened. This has the advantage of giving the operator an efficient way to change the reaction time. Alternatively the release of the first and second reagents can be varied to change the reaction time along the tube. Preferably both the tube length and the release of the first and second reagents can be varied to provide precise control of reaction times.

Preferably the length of the tube can be selected from at least 2 predetermined lengths, preferably from 2 to about 10 predetermined lengths, preferably from about 3 to about 8 predetermined lengths, most preferably from about 4 to about 6 predetermined lengths. By having predetermined lengths, the operator can easily calculate the reaction time. Further, the provision of predetermined lengths makes it easy to automate the selection of the length of the tube.

Preferably the length of the tube or each tube is independently selected from about 1 cm to about 30 cm, preferably from about 5 cm to about 20 cm, most preferably from about 5 cm to about 10 cm. Such tube lengths are suitable for carrying out the required reaction. Preferably each tube has a different length.

Preferably the diameter of the bore of the tube is about 0.2 mm to about 2 mm, preferably about 0.5 mm to about 1.5 mm preferably about 0.75 mm to about 1 mm. The diameter is measured as the widest point in the cross-section of the bore of the tube. Such diameters allow the first reagent and the second reagent to have fast flow rates with low back-pressure.

Preferably the reaction area comprises a pathway extension valve, wherein adjusting the pathway extension valve varies the length of the reaction area fluid pathway. Preferably the pathway extension valve is adjusted by turning. Turning the valve is a suitable way to change the length of the reaction area fluid pathway. Preferably the pathway extension valve comprises a single valve.

Preferably the pathway extension valve comprises a passageway and adjusting the pathway extension valve varies the length of the passageway.

Preferably the pathway extension valve comprises at least one passageway extension, preferably about 2 to about 10 passageway extensions, preferably about 3 to about 8 passageway extensions, preferably about 4 to about 6 passageway extensions. By having passageway extensions of known length, the operator can easily calculate the reaction time. Preferably the passageway extensions are each in the form of a loop.

Further, the provision of passageway extensions makes it easy to automate the selection of the length of the passageway. The provision of one passageway extension gives two different options for the length of the passageway, a shorter passageway which does not include the passageway extension and a longer passageway that does include the passageway extension.

Preferably the pathway extension valve comprises at least two passageway extensions, wherein the pathway extension valve is adjustable to a position where the reaction fluid area pathway comprises at least two passageway extensions. The provision of two passageway extensions, gives three potential different lengths of the passageway, one which does not include any passageway extensions, one which includes a first passageway extension, and one which includes both the first and second passageway extensions. It will be appreciated that the more passageway extensions that are present, the more options for different passageway lengths that are possible.

Preferably each subsequent passageway extension is added to reaction fluid pathway in addition to the previous passageway extensions, for example where a second passageway extension forms part of the reaction fluid pathway, the first passageway extension also forms part of the reaction area fluid pathway. This means that the length of the reaction area fluid pathway is increased by adding additional passageway extensions.

Preferably each passageway extension is about the same length, preferably the same length. Alternatively, passageway extension may be a different length. The length of the passageway can be varied by including the first passageway extension or the first passageway extension and further passageway extensions. The addition of each passageway extension into the reaction area fluid pathway by adjusting the pathway extension valve will increase the length of the passageway and thus the reaction area fluid pathway. Preferably, adjusting the valve varies the number of passageway extensions that form part of the reaction area fluid pathway.

In one embodiment, some of the passageway extensions may be about the same length, and others may be a different length. Such an arrangement would give flexibility to the operator to select an appropriate length.

Preferably the length of the or each passageway extension is independently selected from about 1 cm to about 30 cm, preferably from about 5 cm to about 20 cm, most preferably from about 5 cm to about 10 cm. Such passageway extension lengths are suitable for carrying out the required reaction.

Preferably the length of the passageway through the pathway extension valve, including any passageway extensions is 1 cm to 120 cm, preferably 1 cm to 100 cm, preferably 2 cm to 50 cm.

Preferably the diameter of the bore of the or each passageway extension is about 0.2 mm to about 2 mm, preferably about 0.5 mm to about 1.5 mm preferably about 0.75 mm to about 1 mm. The diameter is measured as the widest point in the cross-section of the bore of the passageway extension. Such diameters allow the first reagent and the second reagent to have fast flow rates with low back-pressure.

Preferably the diameter of the bore of the passageway is about 0.2 mm to about 2 mm, preferably about 0.5 mm to about 1.5 mm preferably about 0.75 mm to about 1 mm. The diameter is measured as the widest point in the cross-section of the bore of the passageway extension. Such diameters allow the first reagent and the second reagent to have fast flow rates with low back-pressure.

Preferably, the diameter of the bore of each passageway extension is the same as the diameter of the bore of the passageway.

Preferably the passageway comprises a tube. Preferably the passageway extensions comprise a tube. An advantage of a tube is that it allows controlled mixing of the first and second reagents and the reaction can flow along the tube to be quenched, if required. This means that the reaction will be aged in a controlled manner, as the first and second reagents are continuously released into the tube at a known rate. A tube also allows the result of the reaction to be quenched after a predetermined time as the reaction occurs along the tube. Preferably the tube is flexible, such that it can bend in a loop.

The passageway may comprise a channel. The passageway extensions may comprise a channel. A channel may be formed through a solid material, such as a thermoplastic, whereby a channel is cast or tooled into the solid material to allow fluid to flow along the channel. Alternatively, the pathway extension valve, including the channels may be printed by a 3D printer. An advantage of a channel is that it allows controlled mixing of the first and second reagents and the reaction can flow along the channel to be quenched, if required. This means that the reaction will be aged in a controlled manner, as the first and second reagents are continuously released into the channel at a known rate. A channel also allows the result of the reaction to be quenched after a predetermined time as the reaction occurs along the channel. Furthermore, a channel through a solid material has structural rigidity provided by the solid material.

Preferably the cross-section of the tube or the channel is substantially circular. Such a cross-section reduces the forces imparted to the reaction liquid and helps to ensure an even flow of the reagents through the reaction area. Alternatively, the cross-section may be non-circular, such as elliptical, triangular, square or rectangular.

Preferably the cross-sectional area of the tube or the channel varies by less than about 20% of the mean average cross-sectional area along the length of the tube, such as 0% to about 20%, or about 1% to about 20%, preferably less than about 10%, preferably less than about 5%, preferably less than about 2%, preferably less than about 1%, most preferably no variation.

Preferably the quenching area comprises a mixer. The mixer may be any fluid mixer, such as a t format mixer or a berger ball. The mixer helps the reaction to be quenched in a controlled manner.

Preferably the system further comprises an analysis apparatus in fluid communication with the HPLC apparatus, preferably a mass spectrometer, a UV detector, a VIS detector, a PDA detector, a nuclear magnetic resonance spectrometer, a refractive index detector, a evaporative light scattering detector, a multi-angle light scattering detector, a conductivity detector, a fluorescence detector, a chemiluminescence detector, an optical rotation detector, an electro chemical detector, preferably a mass spectrometer. This allows the quenched flow reaction liquid to be further analysed and for this process to be automated.

The system preferably comprises valves which each independently control the release of the first reagent, the second reagent and the quenching reagent. The system preferably comprises valves which each independently control the release of the first precursor and the second precursor. Further, valves can be used throughout the system to control the release of the reagents and quenched flow reaction liquid. Further, valves can be used throughout the system to control the release of the precursors.

The system preferably contains a buffer release mechanism. The buffer release mechanism when actuated can be used to push buffer through the system and move the quenched flow reaction liquid through the system without using excess first reagent, second reagent and quenching reagent. The buffer release mechanism can also be used to wash through the system between reactions. Preferably the buffer release mechanism is automated. Preferably the buffer release system is a syringe, preferably a syringe actuated by a stepper-motor control drive. The buffer release mechanism may be an injector valve. Preferably there is more than one buffer release mechanism. This allows buffer to be used to move liquid through the system. Preferably any or all of the quenched flow reaction liquid, first precursor, second precursor, first reagent or second reagent may be moved through the system by buffer from one or more buffer release mechanisms.

Once the reaction has been quenched, any of the first reagent, second reagent, quenching reagent and buffer may be used to move the quenched flow reaction liquid through the system to the HPLC apparatus for analysis. Further, the first precursor and/or the second precursor may be used to move the quenched flow reaction liquid through the system to the HPLC apparatus for analysis The present invention relates to a method for analysing the composition of a quenched flow reaction liquid comprising:
(a) providing a first reagent,
(b) providing a second reagent,
(c) mixing the first reagent and the second reagent in a reaction area,
(d) allowing a reaction to take place between the first reagent and the second reagent in the reaction area for a predetermined reaction time,
(e) quenching the reaction in a quenching area to form a quenched flow reaction liquid,
(f) directly transferring a proportion of the quenched flow reaction liquid into a HPLC apparatus, and
(g) analysing the quenched flow reaction liquid by HPLC to form an HPLC analyte.

Preferably the steps are sequential.

Preferably step (f) comprises transferring the quenched flow reaction liquid from the quenched flow reactor through a bypass valve, and adjusting the bypass valve to a first position to transfer a first proportion of the quenched flow reaction liquid to a non-HPLC apparatus location and adjusting the bypass valve to a second position to transfers a second proportion of the quenched flow reaction liquid into the HPLC apparatus. Preferably the non-HPLC location is to waste. Alternatively the non-HPLC location is to a container and the first proportion of the quenched flow reaction liquid is further used, such as for analysis.

Preferably the second proportion of the quenched flow reaction liquid is transferred into a HPLC injector valve of the HPLC apparatus, preferably into a HPLC injection valve loop.

The bypass valve allows the operator to direct part of the quenched flow reaction liquid that does not need to be analysed out of the system, when the bypass valve is in a first position. This allows a high flow rate to be used in the quenched flow reactor, such as about 0.2 ml/s to about 30 ml/s, preferably about 0.5 ml/s to about 20 ml/s whilst the reaction is taking place, and allows the first proportion of the quenched flow reaction liquid to be removed from the system at such a high flow rate and minimises any back pressure in the system. Preferably the first proportion of the quenched flow reaction liquid is removed via tubing with a wide bore, preferably about 0.5 mm to about 1.5 mm.

The bypass valve can then be moved into a second position which directs the second proportion of the quenched flow reaction liquid into the HPLC injection valve, and in particular into the HPLC injection valve loop. The HPLC injection valve loop preferably has a smaller bore than that of the tube in the quenched flow reactor. This is due to the higher pressure required for the HPLC apparatus. The flow rate through the HPLC apparatus is preferably about 5 µl/s to about 250 µl/s, preferably about 10 µl/s to about 100 µl/s which is considerably lower than the flow rate through the quenched flow reactor when the first reagent and second reagent are mixed. It is therefore preferable for the flow rate through the system to be about 0.2 to about 30 ml/s, such as about 0.5 to about 20 ml/sup until the reagents have mixed, preferably until the reaction is quenched, with the bypass valve in the first position to remove the first proportion of the quenched flow reaction liquid. It is preferable for the flow rate through the system to be about 5 µl/s to about 250 µl/s, preferably about 10 µl/s about 100 µl/s after the reaction has been quenched, with the bypass valve in the second position to load the second proportion of the quenched flow reaction liquid into the HPLC injection valve loop, ready for analysis. The bypass valve has the advantage of allowing fast flow rates through the system while the reaction is occurring, with lower flow rates through the system to load the HPLC injection valve loop.

It will be appreciated that the system is preferably primed with buffer to allow a smooth path of the reagents through the system. The buffer preferably exits the system via the bypass valve in the first position. It is therefore possible for only buffer to exit the system when the bypass valve is in the first position and then the quenched flow reaction liquid to be piped into the HPLC injection valve. Usually, at least some of the quenched flow reaction liquid exits the system through the bypass valve in the first position to ensure the best sample is analysed by HPLC.

Preferably the quenched flow reaction liquid is piped from the quenched flow reactor through the bypass valve.

The HPLC injection valve allows the pressure of the quenched flow reaction liquid to be changed from low pressure, such as about 0 psi to about 200 psi in the quenched flow reactor, to about 2,000 psi to about 20,000 psi in the column of the HPLC apparatus. The pressure differential between the two apparatus is necessary for each to carry out their normal function.

Preferably the HPLC injection valve comprises a HPLC injection valve loop for holding a first part of the second proportion of the quenched flow reaction liquid prior to injecting the first part of the second proportion of the quenched flow reaction liquid into the column. This allows the operator to select the proportion of the quenched flow reaction liquid to be analysed. The HPLC injection valve loop can then be moved inline with the solvent of the HPLC apparatus to push the first part of the second proportion of the quenched flow reaction liquid onto the column for analysis. The first part of the second proportion of the quenched flow reaction liquid may be all of the second proportion of the quenched flow reaction liquid.

Preferably, the first part of the second proportion of the quenched flow reaction liquid is not all of the second proportion of the quenched flow reaction liquid. This allows some of the first part of the second proportion of the quenched flow reactor to be removed from the system, such as to waste, or to a container for further analysis. The ability of the HPLC injector valve to select which of the quenched flow reaction liquid is held in the HPLC injection valve loop increases the control the operator has to carry out the analysis.

Preferably the diameter of the bore of the HPLC injection valve loop is about 0.05 mm to about 0.5 mm, preferably about 0.1 mm to about 0.4 mm, preferably about 0.2 mm to about 0.3 mm. Such diameters are suitable to withstand the high pressure required for the column, such as about 2,000 psi to about 20,000 psi.

Preferably step (a) comprises providing a prereaction system, preferably wherein the prereaction system comprises:
A. providing a first precursor,
B. providing a second precursor,
C. mixing the first precursor and the second precursor in a prereaction area,
D. allowing a prereaction to take place between the first precursor and the second precursor in the prereaction area for a predetermined prereaction time, to form the first reagent.

It will be appreciated that the first reagent, the second reagent, the first precursor and the second precursor may comprise more than one component.

Preferably the prereaction causes a detectable change to the first and/or second precursor.

Preferably the reaction causes a detectable change to the first and/or second reagent.

Preferably the first reagent comprises a macromolecule, more preferably wherein the first reagent comprises a protein or a fragment domain or subunit thereof. Preferably the macromolecule comprises multiple protein subunits. Analysis of a macromolecule, such as a protein is highly desirable due to their complex make up.

Preferably the first precursor comprises a macromolecule, more preferably wherein the first precursor comprises a protein or a fragment domain or subunit thereof. Preferably the macromolecule comprises multiple protein subunits. Preferably the second precursor comprises a ligand. This allows the binding of a ligand to a macromolecule to be analysed.

Preferably the second reagent comprises (i) a label, or (ii) induces a measurable change in the first reagent. This is particularly useful when analysing a large complex structure, such as a macromolecule and in particular a protein. This technique may also be used to analyse other molecules, or other compositions.

Preferably the second reagent comprises deuterium oxide. Deuterium oxide is a useful reagent to use for analysing molecules, such as macromolecules, and particularly proteins. The hydrogen and deuterium exchange that occurs helps analyse the external surface of such a structure. The reaction time needs to be carefully controlled for optimum analysis. Fast Hydrogen-Deuterium Exchange (HDX) is a valuable tool in analysing proteins, and the present invention allows very fast reaction times to be analysed as described below. In particular, the method of the invention allows the quenched flow reaction liquid to enter the HPLC apparatus for analysis within seconds, such as about 0.5 s to about 10 s. This is particularly important for HDX as typically the reaction is not completely quenched, and any delay in moving the quenched flow reaction liquid increases the chance of back exchange of the deuterium and hydrogen. Such back-exchange is minimised by the present invention.

An advantage of using a prereaction to take place between the first precursor and the second precursor is that it is possible to vary both the reaction time and the prereaction time to analyse the extent of the prereaction and the extent of the reaction. This is particularly useful for analysing the prereaction of, for example, a macromolecule with a ligand, by controlling the prereaction and then analysing the allosteric changes, such as using HDX. Analysis of a macromolecule, such as a protein, in combination with a ligand is highly desirable due to the complex nature of their interactions.

It has surprisingly been found that the present invention allows a wide range of reaction times to be carried out, such as about 5 ms to about 24 hours, preferably about 10 ms to about 12 hours, preferably about 20 ms to about 3 hours, preferably about 50 ms to about 1 hour, preferably about 100 ms to about 30 minutes, preferably about 200 ms to about 1 minutes, preferably about 250 ms to about 10 s, preferably about 500 ms to about 1 s. It is particularly useful to be able to carry out in line analysis of several time points of the reaction to determine the extent of reaction. Representative time points are about 30 ms, about 100 ms, about 200 ms, about 500 ms, about 1 s, about 2 s, about 10 s.

The reaction time can be less than about 10 s, preferably less than about 2 s, preferably less than about 1 s, preferably less than about 500 ms, preferably less than about 200 ms, preferably less than about 100 ms, preferably less than about 30 ms.

Preferably in step (a) the first reagent is provided at a first rate. Preferably in step (b) the second reagent is provided at a second rate. The relative rates of release can be used to help control the extent of the reaction. The first rate and the second rate may be the same, or different. The first rate and the second rate can each independently vary during the reaction. In particular, once the first reagent and second reagent have mixed, the rate of release of the first reagent and second reagent can be reduced, or even stopped to allow a longer reaction time. The first and second rate could then be increased to push the reaction into the quenching area. Alternatively, a buffer may be provided to push the reaction into the quenching area.

Preferably the first reagent in step (a) is provided in a syringe. Preferably the second reagent in step (b) is provided in a syringe. Preferably both the first reagent and the second reagent are provided in a syringe. A syringe allows controlled release of each reagent in a predetermined manner. Further this allows a reaction time of the order of milliseconds to be achieved.

Preferably the first reagent and the second reagent each independently provided in a syringe actuated by a stepper-motor control drive.

Alternatively, the first reagent may be provided via an injector valve. The second reagent may be provided via an injector valve. In some embodiments each of the first reagent and the second reagent are provided via an injection valve. An injector valve provides an efficient way to introduce different reagents into the system. In particular, where several samples need to be analysed, it can be preferable for the first reagent release mechanism to be an injection valve.

Preferably the actuation of the syringe containing the first reagent is automated. Preferably the actuation of the syringe containing the second reagent is automated. Preferably actuation of the syringe containing the first reagent and the syringe containing the second reagent is automated. Automation allows the operator to program the required reagent release start and end time, together with the release rate to accurately carry out the reaction. Further this allows a reaction time of the order of milliseconds to be achieved. Further this allows efficient use of the equipment. Further this leads to reproduceable results as the time from the reaction starting, to the reaction being quenched, to the analysis stage is consistent.

Preferably the prereaction has one or more features of the reaction as described herein. Preferably the prereaction area has one or more features of the reaction area as described herein. Preferably the prereaction area fluid pathway has one or more features of the reaction area fluid pathway as described herein. Preferably the first precursor is provided as described herein for the first reagent. Preferably the second precursor is provided as described herein for the second reagent Preferably the HPLC apparatus comprises a HPLC injection valve and a column, preferably wherein the column is a digestion column. Preferably the digestion column is a pepsin column. A digestion column allows macromolecules, such as proteins to be digested.

Preferably about 5% to about 80% by volume of the quenched flow reaction liquid is directed into the HPLC apparatus, preferably about 10% to about 50% by volume. Such amounts are suitable to ensure that the quenched flow reaction liquid of an accurate reaction time and first reagent to second reagent ratio enters the HPLC apparatus.

Preferably the second proportion of the quenched flow reaction liquid directed into the HPLC apparatus is adjustable. This has the advantage of being able to control the amount of sample entering the HPLC apparatus.

Preferably the reaction area comprises a tube. An advantage of tube is that it allows controlled mixing of the first and second reagents and the reaction can flow along the tube to be quenched. This means that the reaction will be aged in a controlled manner, as the first and second reagents are continuously released into the tube at a known rate. A tube also allows the result of the reaction to be quenched after a predetermined time as the reaction occurs along the tube. Preferably the reaction area comprises a mixer and a tube. Preferably the mixer is at the start of the tube. The mixer may be any fluid mixer, such as a t format mixer. The combination of a mixer and a tube helps the reaction to be carried out in a controlled manner.

Preferably the length of the tube can be varied. Varying the length of the tube means that the length of the reaction time can be easily changed as the reaction area is shortened or lengthened. This has the advantage of giving the operator an efficient way to change the reaction time. Alternatively the release of the first and second reagents can be varied to change the reaction time along the tube. Preferably both the tube length and the release of the first and second reagents can be varied to provide precise control of reaction times.

Preferably the length of the tube can be selected from at least 2 predetermined lengths, preferably from 2 to about 10 predetermined lengths, preferably from about 3 to about 8 predetermined lengths, most preferably from about 4 to about 6 predetermined lengths. By having predetermined lengths, the operator can easily calculate the reaction time. Further, the provision of predetermined lengths makes it easy to automate the selection of the length of the tube.

Preferably the length of the tube or each tube is independently selected from about 1 cm to about 30 cm, preferably from about 5 cm to about 20 cm, most preferably from about 5 cm to about 10 cm. Such tube lengths are suitable for carrying out the required reaction. Preferably each tube has a different length.

Preferably the diameter of the bore of the tube is about 0.2 mm to about 2 mm, preferably about 0.5 mm to about 1.5 mm preferably about 0.75 mm to about 1 mm. The diameter is measured as the widest point in the cross-section of the bore of the tube. Such diameters allow the first reagent and the second reagent to have fast flow rates with low backpressure.

Preferably the reaction area comprises a pathway extension valve, wherein adjusting the pathway extension valve varies the length of the reaction area fluid pathway. Preferably the pathway extension valve is adjusted by turning. Turning the valve is a suitable way to change the length of the reaction area fluid pathway. Preferably the pathway extension valve comprises a single valve.

Preferably the pathway extension valve comprises a passageway and adjusting the pathway extension valve varies the length of the passageway.

Preferably the pathway extension valve comprises at least one passageway extension, preferably about 2 to about 10 passageway extensions, preferably about 3 to about 8 passageway extensions, preferably about 4 to about 6 passageway extensions. By having passageway extensions of known length, the operator can easily calculate the reaction time. Preferably the passageway extensions are each in the form of a loop.

Further, the provision of passageway extensions makes it easy to automate the selection of the length of the passageway. The provision of one passageway extension gives two different options for the length of the passageway, a shorter passageway which does not include the passageway extension and a longer passageway that does include the passageway extension.

Preferably the pathway extension valve comprises at least two passageway extensions, wherein the pathway extension valve is adjustable to a position where the reaction fluid area pathway comprises at least two passageway extensions. The provision of two passageway extensions, gives three potential different lengths of the passageway, one which does not include any passageway extensions, one which includes a first passageway extension, and one which includes both the first and second passageway extensions. It will be appreciated that the more passageway extensions that are present, the more options for different passageway lengths that are possible.

Preferably each subsequent passageway extension is added to reaction fluid pathway in addition to the previous passageway extensions, for example where a second passageway extension forms part of the reaction fluid pathway, the first passageway extension also forms part of the reaction area fluid pathway. This means that the length of the reaction area fluid pathway is increased by adding additional passageway extensions.

Preferably each passageway extension is about the same length, preferably the same length. Alternatively, passageway extension may be a different length. The length of the passageway can be varied by including the first passageway extension or the first passageway extension and further passageway extensions. The addition of each passageway extension into the reaction area fluid pathway by adjusting the pathway extension valve will increase the length of the passageway and thus the reaction area fluid pathway. Preferably, adjusting the valve varies the number of passageway extensions that form part of the reaction area fluid pathway.

In one embodiment, some of the passageway extensions may be about the same length, and others may be a different length. Such an arrangement would give flexibility to the operator to select an appropriate length.

Preferably the length of the or each passageway extension is independently selected from about 1 cm to about 30 cm, preferably from about 5 cm to about 20 cm, most preferably from about 5 cm to about 10 cm. Such passageway extension lengths are suitable for carrying out the required reaction.

Preferably the length of the passageway through the pathway extension valve, including any passageway extensions is 1 cm to 120 cm, preferably 1 cm to 100 cm, preferably 2 cm to 50 cm.

Preferably the diameter of the bore of the or each passageway extension is about 0.2 mm to about 2 mm, preferably about 0.5 mm to about 1.5 mm preferably about 0.75 mm to about 1 mm. The diameter is measured as the widest point in the cross-section of the bore of the passageway extension. Such diameters allow the first reagent and the second reagent to have fast flow rates with low back-pressure.

Preferably the diameter of the bore of the passageway is about 0.2 mm to about 2 mm, preferably about 0.5 mm to about 1.5 mm preferably about 0.75 mm to about 1 mm. The diameter is measured as the widest point in the cross-section of the bore of the passageway extension. Such diameters allow the first reagent and the second reagent to have fast flow rates with low back-pressure.

Preferably, the diameter of the bore of each passageway extension is the same as the diameter of the bore of the passageway.

Preferably the passageway comprises a tube. Preferably the passageway extensions comprise a tube. An advantage of a tube is that it allows controlled mixing of the first and second reagents and the reaction can flow along the tube to be quenched, if required. This means that the reaction will be aged in a controlled manner, as the first and second reagents are continuously released into the tube at a known rate. A tube also allows the result of the reaction to be quenched after a predetermined time as the reaction occurs along the tube. Preferably the tube is flexible, such that it can bend in a loop.

The passageway may comprise a channel. The passageway extensions may comprise a channel. A channel may be formed through a solid material, such as a thermoplastic, whereby a channel is cast or tooled into the solid material to allow fluid to flow along the channel. Alternatively, the pathway extension valve, including the channels may be printed by a 3D printer. An advantage of a channel is that it allows controlled mixing of the first and second reagents and the reaction can flow along the channel to be quenched, if required. This means that the reaction will be aged in a controlled manner, as the first and second reagents are continuously released into the channel at a known rate. A channel also allows the result of the reaction to be quenched after a predetermined time as the reaction occurs along the channel. Furthermore, a channel through a solid material has structural rigidity provided by the solid material.

Preferably the cross-section of the tube or the channel is substantially circular. Such a cross-section reduces the forces imparted to the reaction liquid and helps to ensure an even flow of the reagents through the reaction area. Alternatively, the cross-section may be non-circular, such as elliptical, triangular, square or rectangular.

Preferably the cross-sectional area of the tube or the channel varies by less than about 20% of the mean average cross-sectional area along the length of the tube, such as 0% to about 20%, or about 1% to about 20%, preferably less than about 10%, preferably less than about 5%, preferably less than about 2%, preferably less than about 1%, most preferably no variation.

Preferably the reaction is quenched in step (e) by providing a quenching reagent. Preferably the quenching reagent in step (e) is provided in a syringe. A syringe allows controlled release of each reagent in a predetermined manner. Further this allows a reaction time of the order of milliseconds to be achieved.

Preferably the quenching reagent is provided in a syringe actuated by a stepper-motor control drive.

Alternatively, the quenching reagent may be provided via an injector valve. An injector valve provides an efficient way to introduce different quenching reagents into the system.

Preferably the actuation of the syringe containing the quenching reagent is automated. Automation allows the operator to program the required reagent release start and end time, together with the release rate to accurately carry out the reaction. Further this allows a reaction time of the order of milliseconds to be achieved. Further this allows efficient use of the equipment. Further this leads to reproduceable results as the time from the reaction starting, to the reaction being quenched, to the analysis stage is consistent.

Preferably in step (e) the reaction is quenched by cooling. Alternatively, in step (e) the reaction is quenched by heating. The temperature change is preferably provided by adding a quenching reagent at an appropriate temperature.

Preferably in step (e) the reaction is quenched by adding a quenching reagent, preferably an acid or a base, preferably an acid, preferably formic acid.

Preferably in step (e) the reaction is quenched by both cooling and adding a quenching reagent. In particular, where deuterium oxide is the second reagent, the reaction is preferably quenched by adding acid, preferably formic acid at a temperature of about 0.1° C. to about 5° C., such as about 1° C. to about 3° C.

Alternatively, in step (e) the reaction is quenched by both heating and adding a quenching reagent.

The skilled person will appreciate that the reaction time can be set by adjusting one or more parameters relating to the reaction. These include the release rate of the first reagent and the second reagent, the size of the reaction area, such as the length of the tube and the point at which the reaction is quenched.

The volume of the first reagent, second reagent and quenching reagent may each independently be from about 0.01 ml to about 2.5 ml, preferably from about 0.02 ml to about 0.250 ml. Further, the volume of the first precursor and the second precursor may each independently be from about 0.01 ml to about 2.5 ml, preferably from about 0.02 ml to about 0.250 ml. Such volumes are appropriate for analysing a molecule such as a macromolecule, particularly a protein as they allow sufficient reaction to occur, whilst minimising the amount of the molecule required to be analysed.

Preferably the HPLC apparatus comprises a digestion column. Preferably the digestion column is a pepsin column. This allows macromolecules, such as proteins to be digested.

Preferably the method further comprises:
(a) directly transferring the HPLC analyte into an analysis apparatus, and
(b) analysing the HPLC analyte by mass spectroscopy.

Preferably the analysis apparatus is a mass spectrometer, a UV detector, a VIS detector, a PDA detector, a nuclear magnetic resonance spectrometer, a refractive index detector, a evaporative light scattering detector, a multi-angle light scattering detector, a conductivity detector, a fluorescence detector, a chemiluminescence detector, an optical rotation detector, an electro chemical detector, preferably a mass spectrometer. This allows the quenched flow reaction liquid to be further analysed and for this process to be automated.

The skilled person will appreciate that the features of the system may be incorporated into the method, and vice versa.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein and vice versa.

Within this specification, the term "about" means plus or minus 20%, more preferably plus or minus 10%, even more preferably plus or minus 5%, most preferably plus or minus 2%.

Within this specification, the term "substantially" means a deviation of up to 20%, more preferably up to 10%, even more preferably up to 5%, most preferably up to 2%.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications are covered by the appended claims.

FIGURES

Example embodiments of the present invention will now be described with reference to the accompanying figures, in which FIG. 1 shows an analysis system of the invention.

Figure 1:
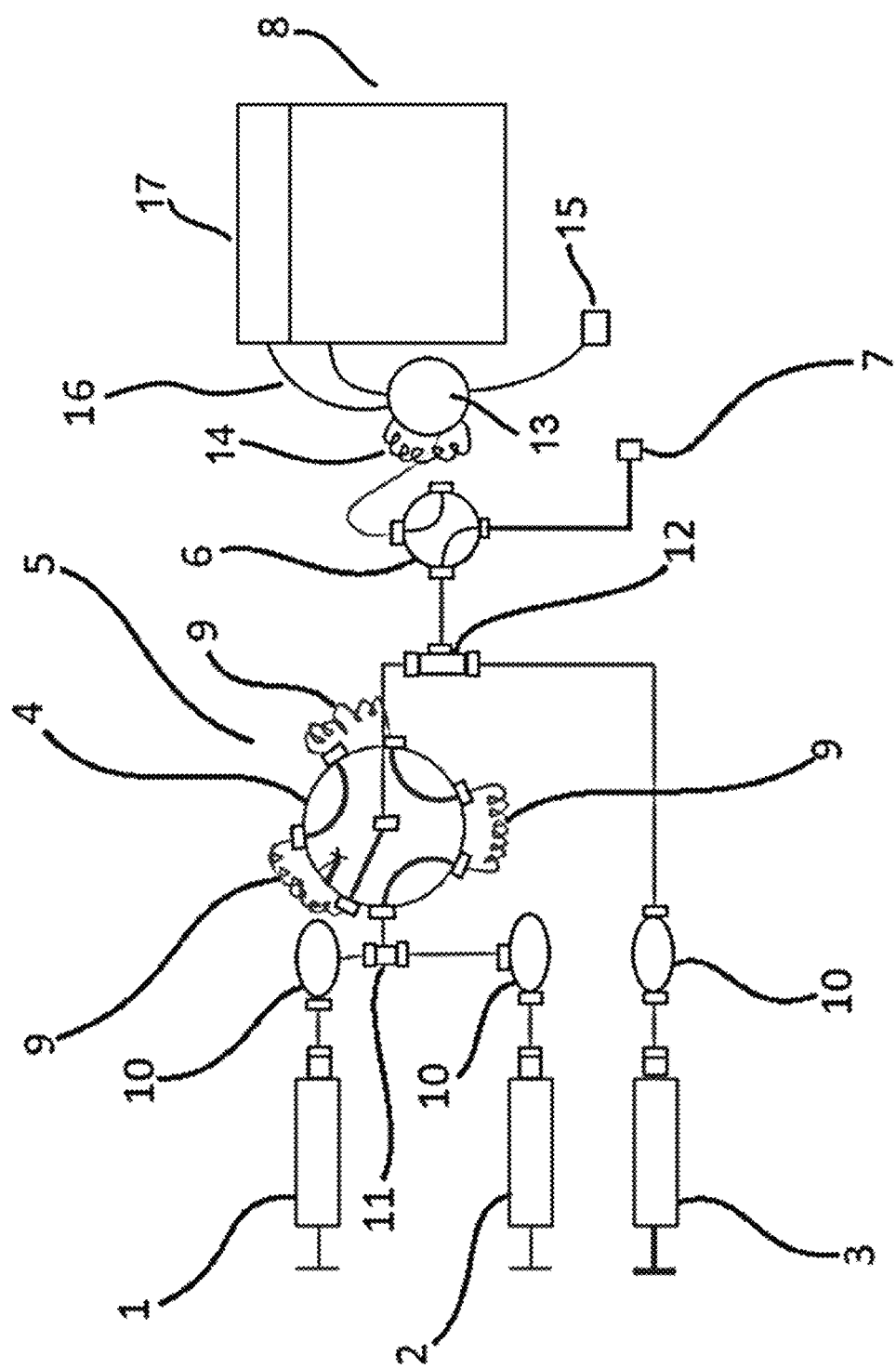

The present invention relates to a system and method for analysing the composition of a quenched flow reaction liquid. FIG. 1 shows a quenched flow reactor 5 in fluid communication with a HPLC apparatus 8. The quenched flow reactor comprises a first reagent release mechanism 1, a second reagent release mechanism 2 and a quenching reagent release mechanism 3. All are shown as a syringe, but other release mechanisms are envisaged. The valve 10 is used to fill the syringe from a reservoir and to allow external delivery of reagents from a separate flow release mechanism.

In use, the first reagent and the second reagent are released and mixed in a reaction area 11 which includes the pathway extension valve 4. Preferably the reaction area 11 comprises a mixer, such as a t-format mixer or a berger ball mixer. The pathway extension valve 4 comprises three loops 9 which may or may not form part of the fluid pathway, depending on the position of the valve. It will be appreciated that other lengths and numbers of option loops are included in the present invention. The liquid then flows to the quenching area 12, where it mixes with the quenching reagent released from the quenching reagent release mechanism 3 to form a quenched flow reaction liquid. The quenching area 12 preferably comprises a mixer, such as a t-format mixer or a berger ball mixer. The quenched flow reaction liquid is then transferred, preferably piped into a bypass valve 6. A first proportion of the quenched flow reaction liquid is then transferred, preferably piped out of the system to waste 7 or to a container 7. This allows the liquid to flow through the quenched flow reactor at a fast rate, such as about 0.2 to about 30 ml/s, preferably about 0.5 to about 20 ml/s while the first reagent and the second reagent are mixing and the reaction is taking place. It will be appreciate that the fast flow rates are required to mix the first reagent and second reagent effectively, and that the flow rates may be reduced, or even stopped to give the desired reaction time, prior to pushing the reaction liquid into the quenching area.

A second proportion of the quenched flow reaction liquid is directed into the HPLC injection valve 13, and in particular through the HPLC injection valve loop 14. The HPLC apparatus 8 comprises a HPLC pump 17 which pumps solvent to the HPLC injection valve 13 through the solvent line 16. The HPLC injection valve loop 14 has two positions. In a first position, the HPLC injection valve loop 14 is connected to waste 15 or to a container 15. This allows the HPLC injection valve loop 14 to be loaded with the desired first part of the second proportion of the quenched flow liquid and some of the quenched flow reaction liquid to be removed from the system. Once the desired first part of the second proportion of the quenched flow reaction liquid is loaded into the HPLC injection valve loop 14, the HPLC injection valve 13 is moved to a second position, in line with the solvent line 16 of the HPLC apparatus to load the selected quenched flow reaction liquid onto the column. The HPLC apparatus 8 may comprise a digestion column, such as a pepsin column. Further, the HPLC analyte resulting from the HPLC analysis may be further piped into an analysis apparatus, preferably a mass spectrometer (not shown).

Figure 2:
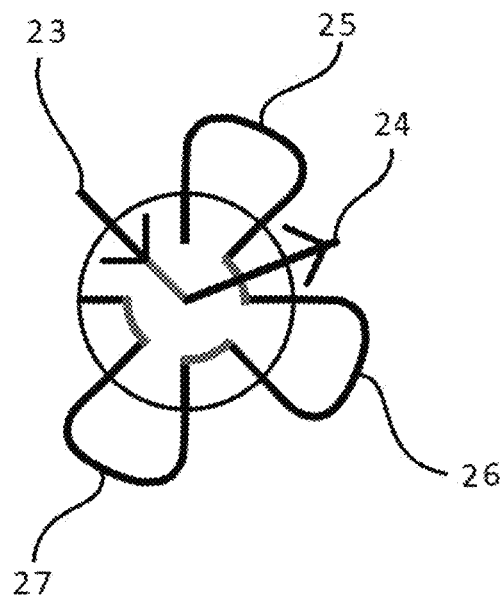
FIG. 2 shows a pathway extension valve in a first configuration.

FIG. 2 shows a pathway extension valve 4 in a first position, whereby the fluid pathway through the pathway extension valve is from the inlet 23, directly to the outlet 24. The additional passageway extensions 25, 26 and 27 do not form part of the passageway at the first position.

Figure 3:
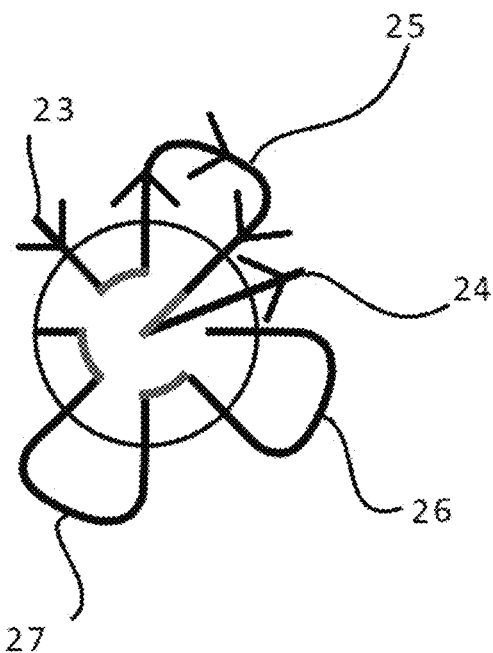
FIG. 3 shows a pathway extension valve in a second configuration.

FIG. 3 shows a pathway extension valve 4 in a second position, whereby the fluid pathway through the pathway extension valve is from the inlet 23, through a first extension passageway 25 and then to the outlet 24. The additional passageway extensions 26 and 27 do not form part of the passageway at the second position.

Figure 4:
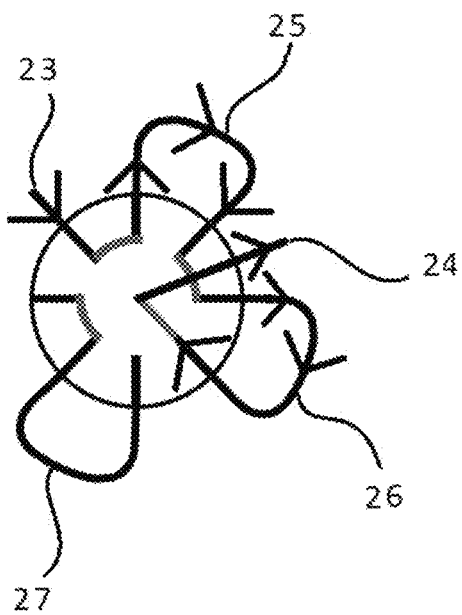
FIG. 4 shows a pathway extension valve in a third configuration.

FIG. 4 shows a pathway extension valve 4 in a third position, whereby the fluid pathway through the pathway extension valve is from the inlet 23, through a first passageway extension 25, through a second passageway extension 26 and then to the outlet 24. The additional passageway extension 27 does not form part of the passageway at the third position.

Figure 5:
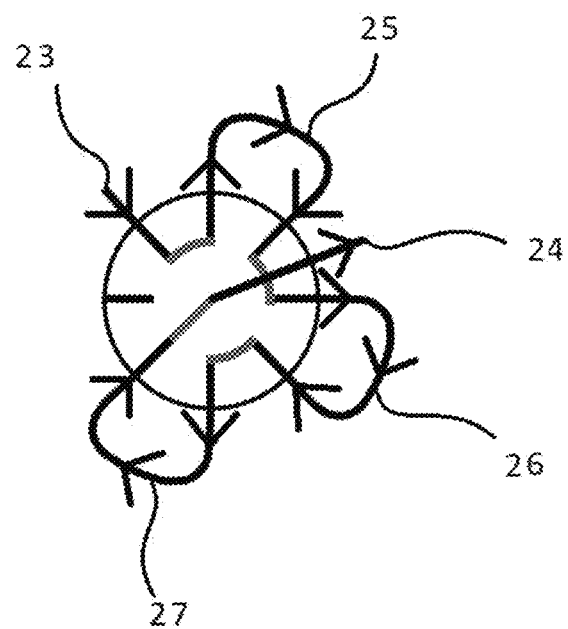
FIG. 5 shows a pathway extension valve in a fourth configuration.

FIG. 5 shows a pathway extension valve 4 in a fourth position, whereby the fluid pathway through the pathway extension valve is from the inlet 23, through a first passageway extension 25, through a second passageway extension 26, through a third passageway extension 27 and then to the outlet 24. There are no unused passageway extensions in the fourth position.

It will be appreciated that each passageway extension is shown as a loop. Each loop may be the same length, or a different length to the other loops present. Further, the length of the passageway through the pathway extension valve can be selected from at least 2 predetermined lengths, preferably from 2 to about 10 predetermined lengths, preferably from about 3 to about 8 predetermined lengths, most preferably from 4 to 6 predetermined lengths. Further, the pathway extension valve may be arranged such that the liquid can flow through a first passageway extension, or a second passageway extension, or a third passageway extension, or a fourth passageway extension, or a fifth passageway extension, or a sixth passageway extension, or a seven passageway extension, or an eight passageway extension, or a ninth passageway extension or a tenth passageway extension, or any combination thereof where each length may be different. It will be appreciated that there may be any number of different passageway extensions in the pathway extension valve, such as at least one, preferably about 2 to about 10, preferably about 3 to about 8, preferably about 4 to about 6.

FIGS. 6a-8b show an example of the pathway extension valve. It will be appreciated that other arrangements are possible, such as a plug type valve with passageway extensions along the radius of the plug and the passageway path diagonally or right angled drilled through the middle of the plug to a common port.

Figure 6A:
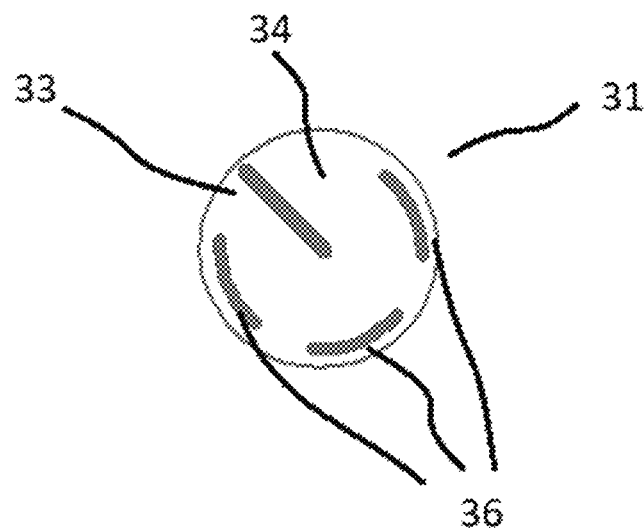
FIG. 6a shows a rotor of a pathway extension valve.

FIG. 6a shows a rotor 31 of a pathway extension valve. The rotor 31 comprises a rotor sealing surface 34. The rotor sealing surface 34 comprises three passageway extensions 36 which may optionally be included in the passageway through the pathway extension valve. The sealing surface further comprises part of the passageway 33.

Figure 6B:
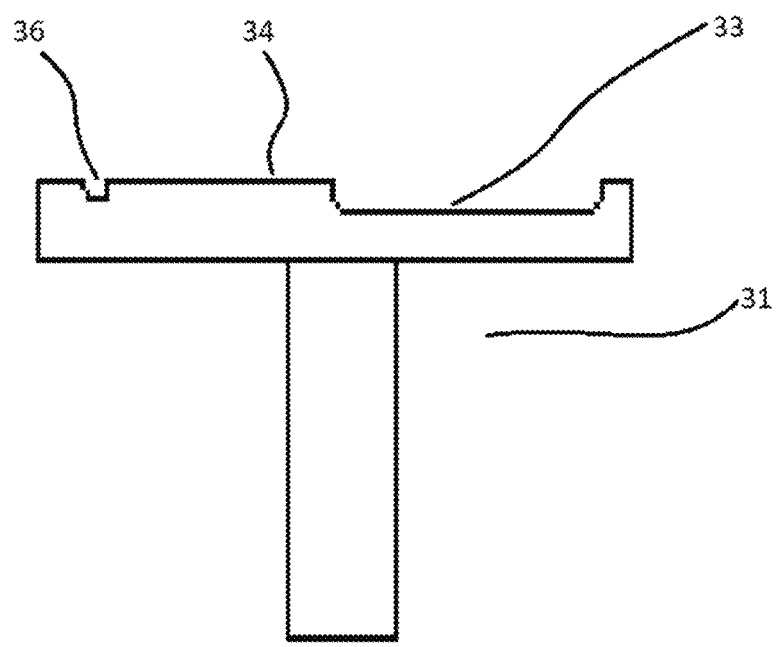
FIG. 6b shows a cross-sectional view of a rotor of a pathway extension valve.

FIG. 6b shows a cross-section view of the rotor 31. One of the passageway extensions 36 and part of the passageway 33 are each shown as an indent in the sealing surface 34.

Figure 7A:
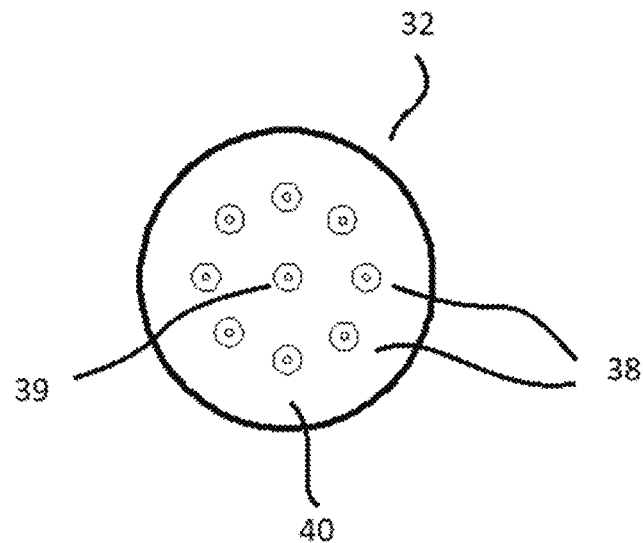
FIG. 7a shows a stator of a pathway extension valve.

FIG. 7a shows a stator 32 of the pathway extension valve. The stator comprises a stator sealing surface 40. The stator sealing surface 40 comprises a plurality of threaded fluid tube sealing ports 38 shown arranged around the outer portion of the stator sealing surface 40. The stator sealing surface 40 has one common threaded fluid tube sealing port 39 shown in the centre of the sealing surface. The common threaded fluid tube sealing port 39 is either the inlet or the outlet. One of the plurality of threaded fluid tube sealing ports 38 is the other of the inlet or the outlet. The arrangement will depend on how the tubing is connected. The stator has a stator sealing surface 40. Adjusting the valve, such as by turning the valve will determine which of the passageway extensions are included in the passageway through the pathway extension valve.

Figure 7B:
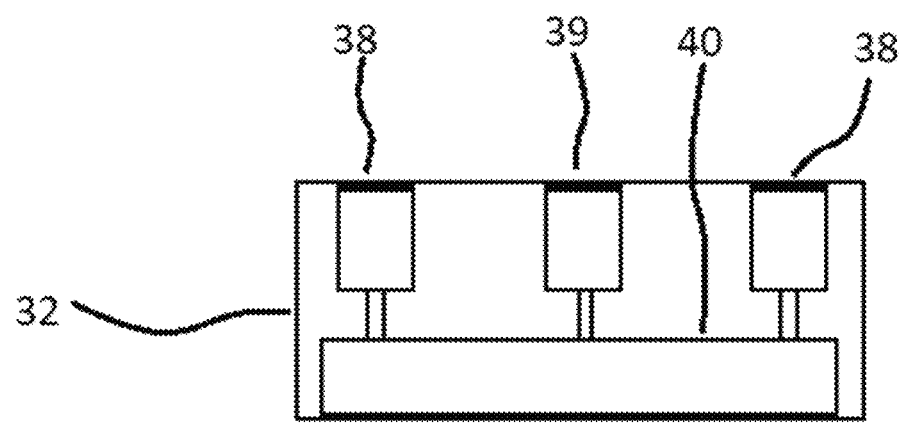
FIG. 7b shows a cross-sectional view of a stator of a pathway extension valve.

FIG. 7b shows a cross-sectional view of the stator 32. The stator sealing surface 40 has threaded fluid tube sealing ports 38 through the surface. The common threaded fluid tube sealing port 39 is shown in the centre of the stator sealing surface 40.

Figure 8A:
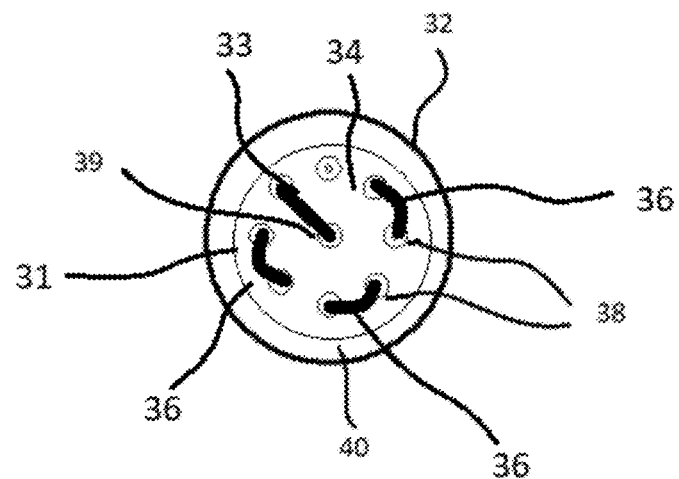
FIG. 8a shows a pathway extension valve.

FIG. 8a shows the rotor 31 in engagement with the stator 32. The threaded fluid tube sealing ports 38 and the common threaded fluid tube sealing port 39 are each engaged with a passageway extension 36 or a part of the passageway 33. The rotor sealing surface engages with the stator sealing surface 40.

Figure 8B:
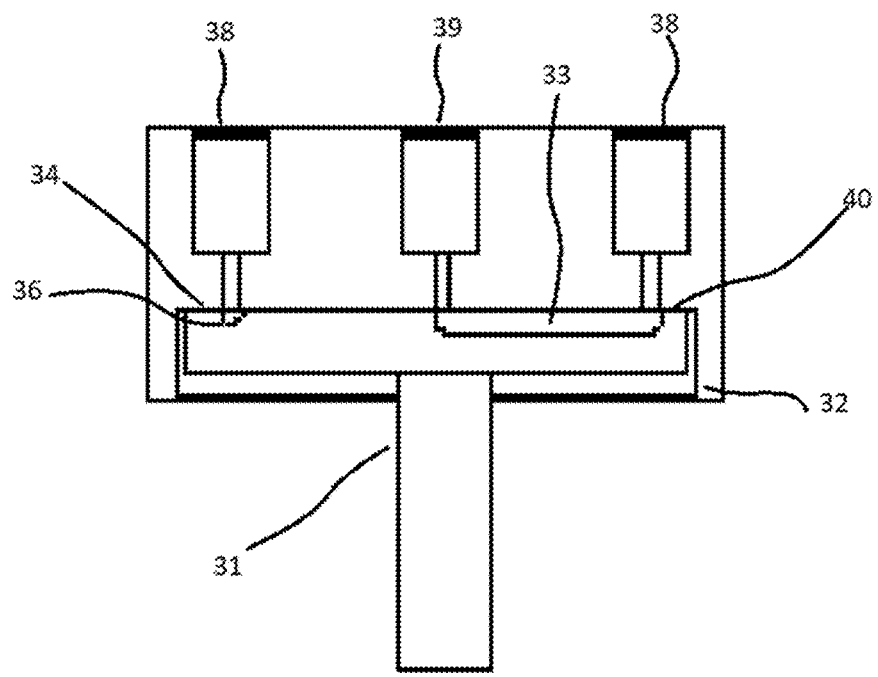
FIG. 8b shows a cross-sectional view of a pathway extension valve.

FIG. 8b shows a cross-sectional view of the rotor 31 in engagement with the stator 32. Part of the passageway 33 lines up with the common threaded fluid tube sealing port 39. Each of the threaded fluid tube sealing ports 38 engage with a passageway extension 36. The rotor sealing surface 34 and the stator sealing surface 40 are in engagement. Adjusting the valve by turning will move the position of the passageway extensions 36 to move them to form part of the passageway or remove them from the passageway, thus allowing the length of the passageway through the pathway extension valve to be adjusted, and thus the length of the reaction area fluid pathway to be changed.

It will be appreciated that the pathway extension valve may have a different number, type and arrangement of sealing ports and tubing.

Figure 9:
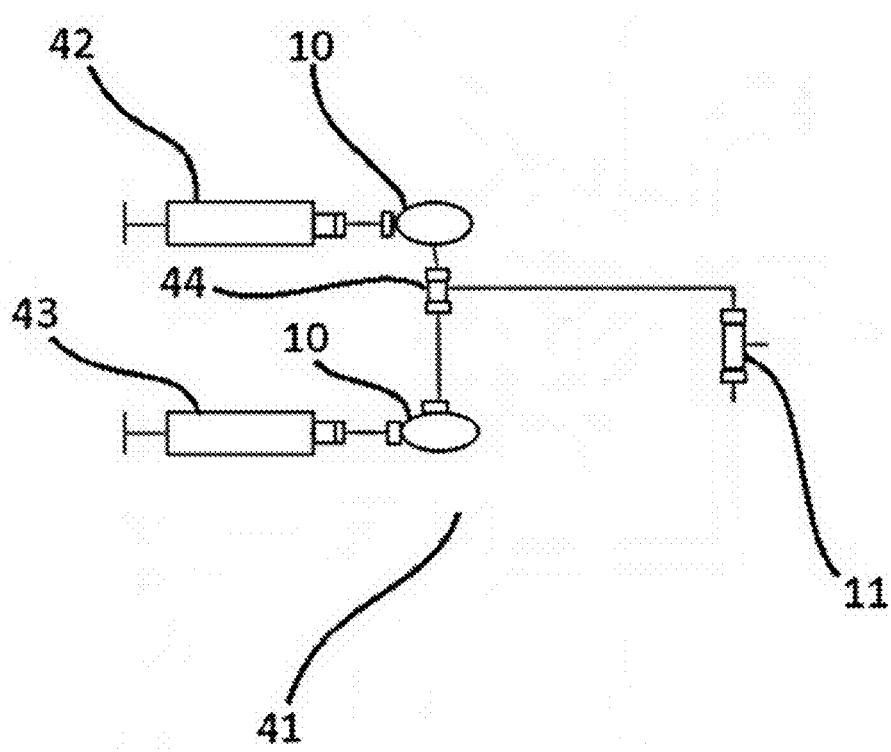
FIG. 9 shows a prereaction system.

FIG. 9 shows a prereaction system 41 that can be optionally incorporated into the quenched flow reactor 5 of FIG. 1. The prereaction system 41 comprises a first precursor release mechanism 42, a second precursor release mechanism 43. All are shown as a syringe, but other release mechanisms are envisaged. The valve 10 is used to fill the syringe from a reservoir and to allow external delivery of reagents from a separate flow release mechanism. In use, the first precursor and the second precursor are released and mixed in a prereaction area 44, to form the first reagent. The prereaction area 44, may preferably comprise a pathway extension valve as described herein (not shown). The first reagent flows to the reaction area 11, where it mixes with the second reagent released from the second reagent release mechanism 2 (not shown). The system and method for analysing the composition of a quenched flow reaction liquid then continues to proceed as described above with reference to FIG. 1.

The invention claimed is:

1. A system for analyzing the composition of a quenched flow reaction liquid comprising a quenched flow reactor, and a high performance liquid chromatography (HPLC) apparatus; wherein the quenched flow reactor is in fluid communication with the HPLC apparatus, wherein the quenched flow reactor and the HPLC apparatus are connected by a bypass valve.

2. The system according to claim 1, wherein the quenched flow reactor comprises:
   a first reagent release mechanism,
   a second reagent release mechanism,
   a reaction area,
   a quenching reagent release mechanism, and
   a quenching area.

3. The system according to claim 2, wherein the first reagent release mechanism is automated and/or wherein the second reagent release mechanism is automated and/or wherein the quenching reagent release mechanism is automated;
   and/or wherein the first reagent release mechanism is a syringe and/or wherein the second reagent release mechanism is a syringe and/or the quenching reagent release mechanism is a syringe.

4. The system according to claim 1, wherein the HPLC apparatus comprises a HPLC injection valve and a column.

5. The system according to claim 4, wherein the HPLC injection valve comprises a HPLC injection valve loop for holding a proportion of the quenched flow reaction liquid prior to injecting the proportion of the quenched flow reaction liquid into the column.

6. The system according to claim 4, wherein in a first position, the bypass valve directs a first proportion of the quenched flow reaction liquid to a non-HPLC apparatus location and wherein in a second position, the bypass valve directs a second proportion of the quenched flow reaction liquid into the HPLC injection valve.

7. The system according to claim 2, wherein the reaction area comprises a tube, and/or wherein the quenching area comprises a mixer.

8. The system according to claim 7, wherein the length of the tube can be varied.

9. The system according to claim 7, wherein the length of the tube can be selected from at least 2 predetermined lengths.

10. The system according to claim 7, wherein the length of the tube or each tube is about 1 cm to about 30 cm.

11. The system according to claim 7, wherein the tube comprises a bore and the diameter of the bore is about 0.2 mm to about 2 mm.

12. The system according to claim 7, wherein the reaction area comprises a pathway extension valve, wherein adjusting the pathway extension valve varies the length of the tube.

13. The system according to claim 1, further comprising an analysis apparatus in fluid communication with the HPLC apparatus.

14. The system according to claim 2, wherein the first reagent release mechanism comprises a prereaction system.

15. A method for analyzing the composition of a quenched flow reaction liquid comprising:
   (a) providing a first reagent,
   (b) providing a second reagent,
   (c) mixing the first reagent and the second reagent in a reaction area,
   (d) allowing a reaction to take place between the first reagent and the second reagent in the reaction area for a predetermined reaction time,
   (e) quenching the reaction in a quenching area to form a quenched flow reaction liquid,
   (f) directly transferring a proportion of the quenched flow reaction liquid into a HPLC apparatus, and
   (g) analyzing the quenched flow reaction liquid by HPLC to form an HPLC analyte, wherein the method is performed in a system according to claim 1.

* * * * *